US006825385B2

(12) United States Patent
Fries et al.

(10) Patent No.: US 6,825,385 B2
(45) Date of Patent: Nov. 30, 2004

(54) PROCESS FOR THE PREPARATION OF ORTHOCARBONATES

(75) Inventors: Guido Fries, Recklinghausen (DE); Jochen Kirchhoff, Luedinghausen (DE)

(73) Assignee: Degussa AG, Duesseldorf (DE)

( * ) Notice: Subject to any disclaimer, the term of this patent is extended or adjusted under 35 U.S.C. 154(b) by 456 days.

(21) Appl. No.: 09/985,759

(22) Filed: Nov. 6, 2001

(65) Prior Publication Data

US 2002/0061984 A1 May 23, 2002

(30) Foreign Application Priority Data

Nov. 17, 2000 (DE) .......................................... 100 57 198

(51) Int. Cl.$^7$ .............................................. C07C 43/32
(52) U.S. Cl. ...................................................... 568/595
(58) Field of Search ........................................ 568/595

(56) References Cited

U.S. PATENT DOCUMENTS 3,876,708 A * 4/1975 Speh et al. .................. 568/591
6,410,745 B1   6/2002 Fries

FOREIGN PATENT DOCUMENTS

| DE | 22 49 460 | 5/1973 |
|----|-----------|--------|
| DE | 22 49 460 | 4/1975 |

OTHER PUBLICATIONS

Derwent Abstracts, AN 1996–369589, KR–9–409936, Oct. 19, 1994.
Derwent Abstracts, AN 1977–65460Y, JP–52–053817, Apr. 30, 1977.
W. Kantlehner, et al., "Die Praeparative chemie der O–and N–funktionelien Othokohiensaeure–Derivate", Synthesis, 1977, pp. 73–90.

* cited by examiner

Primary Examiner—Rita Desai
Assistant Examiner—Robert Shiao
(74) Attorney, Agent, or Firm—Oblon, Spivak, McClelland, Maier & Neustadt, P.C.

(57) ABSTRACT

Orthocarbonates are prepared by a process, comprising:

reacting trichloroacetonitrile with an alkali metal salt or alkaline earth metal salt of an alcohol of the formula:

R—OH                                       (II)

wherein R is an unsubstituted or substituted, saturated aliphatic or cycloaliphatic hydrocarbon radical in which the carbon atom of group R, linked to the oxygen atom of the alcohol, has at least one hydrogen atom, reacting the product obtained in water with an oxidant, extracting the organic-aqueous phase of the material obtained after oxidation, and distilling the extracted material obtained and obtaining orthocarbonate product of the formula:

$C(OR)_4$                                  (I)

wherein each R group is as defined above.

15 Claims, No Drawings

PROCESS FOR THE PREPARATION OF ORTHOCARBONATES

BACKGROUND OF THE INVENTION

1. Field of the Invention

The present invention relates to a process for the preparation of orthocarbonates by reaction of trichloroacetonitrile with an alkali metal salt or alkaline earth metal salt of an alcohol followed by oxidation of the resultant alkali metal cyanide or alkaline earth metal cyanide, extraction of the orthocarbonate, and distillative work-up of the extract.

2. Description of the Background

Orthocarbonates are valuable and versatile intermediates for the synthesis of a wide variety of classes of compound.

For example, OH-acidic compounds such as phenols or carboxylic acids can be etherified or esterified respectively using hydrocarbyl orthocarbonate esters. Furthermore, hydrocarbyl orthocarbonates exhibit characteristic, synthetically valuable reactions with amines, enol ethers, sulfonamides, and the like. (See, in this respect Synthesis 1977, pages 73–90).

Syntheses of orthocarbonates are known as disclosed in the literature. In most processes (see Synthesis 1977, pages 73–90), α-branched radicals, such as, for example, the isopropyl radical, cannot be introduced into the orthocarbonate molecule.

DE-A 22 49 460 indicates a general process specification which can also be used for branched radicals. However, the document discloses that is particularly disadvantageous that the alkali metal chloride or alkaline earth metal chloride and alkali metal cyanide or alkaline earth metal cyanide formed in the reaction of trichloroacetonitrile with an alkali metal salt or alkaline earth metal salt of an alkanol be removed by filtration. Because of the very high toxicity of the cyanide salts, the implementation of high safety measures is necessary. The alkali metal cyanide or alkaline earth metal cyanide formed must subsequently be destroyed or disposed of separately. A need therefore continues to exist for an improved method of synthesizing orthocarbonates.

SUMMARY OF THE INVENTION

Accordingly, one object of the invention is to provide a process for the preparation of orthocarbonates which is technically simple and does not require a filtration step for removal of the salts formed in the reaction of trichloroacetonitrile with an alkali metal salt or alkaline earth metal salt of an alcohol, wherein the alkali metal cyanide or alkaline earth metal cyanide formed is destroyed while still in the reaction batch.

Briefly, this object and other objects of the present invention as hereinafter will become more readily apparent can be attained by a process for the preparation of orthocarbonates, by reacting trichloroacetonitrile with an alkali metal salt or alkaline earth metal salt of an alcohol of the formula:

$$R\text{—}OH \quad (II)$$

wherein R is an unsubstituted or substituted, saturated aliphatic or cycloaliphatic hydrocarbon radical in which the carbon atom of group R, linked to the oxygen atom of the alcohol, has at least one hydrogen atom, in a polar solvent, reacting the product obtained in water with an oxidant, extracting the organic-aqueous phase of the material obtained after oxidation; and distilling the extracted material obtained and obtaining orthocarbonate product of the formula:

$$C(OR)_4 \quad (I)$$

wherein each R group is as defined above.

DETAILED DESCRIPTION OF THE PREFERRED EMBODIMENTS

The objective of the invention is achieved by adding water after the reaction of trichloroacetonitrile with an alkali metal salt or alkaline earth metal salt of an alcohol, extracting the product, and then working-up the product by distillation. Surprisingly, it has been found, in particular, that addition of a mixture of water and oxidant converts the alkali metal cyanide or alkaline earth metal cyanide formed in the reaction in the reaction batch to a nontoxic compound without the conversion resulting in a loss in the yield of orthocarbonate. Thus, the risk potential caused by the presence of an alkali metal cyanide or alkaline earth metal cyanide is reduced to a minimum.

The invention therefore relates to a process for the preparation of orthocarbonates of the general formula $$C(OR)_4 \quad (I)$$

where R is an unsubstituted or substituted, saturated hydrocarbon radical in which the carbon atom linked to the oxygen atom has at least one hydrogen atom, by reaction of trichloroacetonitrile with an alkali metal salt or alkaline earth metal salt of an alcohol of the general formula $$R\text{—}OH \quad (II)$$

where R is as defined above, oxidation of the resultant alkali metal cyanide or alkaline earth metal cyanide, extraction of the orthocarbonate, and distillative work-up of the extract.

In formulas (I) and (II) the substituted or unsubstituted, saturated radical R can be a linear or branched alkyl radical, in particular one having 1 to 7, preferably 1 to 4, carbon atoms, such as, for example, methyl, ethyl, propyl, isopropyl, butyl, isobutyl, pentyl, isopentyl or neopentyl, or a cycloalkyl radical, in particular having 3 to 8 carbon atoms, such as, for example, cyclopropyl, cyclobutyl, cyclopentyl or cyclohexyl, or a cycloalkylalkyl radical, such as, for example, cyclopropylmethyl, cyclopentyl methyl or cyclohexylmethyl. In other words, the carbon atom of the aliphatic group R linked to the oxygen atom of the alcohol compound does not have a hydrogen atom attached thereto. That is, tertiary groups are excluded as aliphatic groups of the alcohol.

In the radicals denoted by R, one or more hydrogen atoms may be replaced by substituents, such as, for example, alkoxy groups, aryloxy groups or dialkyl and/or -aryl-substituted amino groups.

The process for the preparation of orthocarbonates of the present invention comprises the following reaction and process steps:

reaction of trichloroacetonitrile with an alkali metal salt or alkaline earth metal salt of an alcohol of formula R—OH (II), where R is as defined above, addition of water and oxidant, extraction of the orthocarbonate, and distillative work-up of the extract.

The reaction of trichloroacetonitrile with an alkali metal or alkaline earth metal salt of an alcohol of the formula II is conducted in a polar solvent. Examples of suitable solvents include ethers, such as, for example, tetrahydrofuran, dimethoxyethane, diisopropyl ether and dibutyl ether, polyethers, such as, for example, diethylene glycol dimethyl ether, sulfoxides and sulfolanes, such as, for example, dimethyl sulfoxide, sulfolane, 2-methylsulfolane, 3-methylsulfolane and 2-methyl-4-butylsulfolane, nitrites, such as, for example, acetonitrile, amides, such as, for example, dimethylformamide and N,N-dimethylacetamide, and the corresponding alcohols of the formula II. The solvent used is particularly preferably an alcohol of formula II.

The cations in the alkoxide compounds can be alkali metals or alkaline earth metals. Preference is given to sodium alkoxides and potassium alkoxides.

The temperature of the reaction are from −20° C. to 200° C., preferably from 50° C. to 150° C., very particularly preferably the reflux temperature of the reaction mixture.

The reaction of trichloroacetonitrile with alkoxide is conducted at a pressure ranging from 0.1 bar to 50 bar, preferably at a pressure ranging from 1 bar to 10 bar. The reaction is particularly preferably conducted at atmospheric pressure.

The alkoxides are prepared by known methods from the corresponding alcohols of formula II. These alkoxides are known compounds or can be prepared in a manner similar to the methods of preparing analogous, known compounds.

After the reaction, the reaction mixture is preferably stirred at the reflux temperature ranging from 10 minutes to 24 hours, preferably from 1 to 10 hours, very particularly preferably from 2 to 3 hours. The solvent used can, if desired, subsequently be completely removed by distillation. However, preferably, the solvent content is reduced in amount ranging from 10% to 90%, particularly preferably from 70% to 80%.

In order to dissolve the precipitated salt, a sufficient amount of water to which an oxidant has been added is added at a temperature ranging from 0° C. to 90° C., preferably at a temperature ranging from 5° C. to 40° C., on a small scale also particularly preferably at room temperature of about 20° C. Besides chlorine or chlorine water, the oxidant used can also be, for example, polysulfide, thiosulfate, polythionate, hydrogen peroxide, hypochlorite or hypobromite solutions. A hydrogen peroxide solution is particularly preferred. The hydrogen peroxide solution added to the reaction mixture can have a concentration ranging from 0.1 to 70% by weight. A solution having a hydrogen peroxide solution concentration ranging from 3 to 50% by weight is preferred, particularly preferably about 3% strength by weight solution.

The extraction can be conducted continuously or batchwise at temperatures ranging from 0° C. to 100° C., preferably from 0° C. to 50° C., particularly preferably at room temperature of about 15 to 30° C.

Suitable extractants include organic, aprotic solvents. Examples of suitable extractants include aliphatic hydrocarbons, such as, for example, pentane and hexane; cycloaliphatic hydrocarbons, such as, for example, cyclohexane, methylcyclohexane and ethylcyclohexane; aromatic hydrocarbons, such as, for example, toluene, ethylbenzene, xylenes, cumene and mesitylene; chlorinated hydrocarbons, such as, for example, dichloromethane, 1,1- and 1,2-dichloroethane and trichloromethane; ketones, such as, for example, methyl isobutyl ketone, methylcyclohexanone and diisobutyl ketone; and esters, such as, for example, ethyl acetate, butyl acetate and ethyl propionate. The extractant is preferably toluene or cyclohexane or particularly preferably methylcyclohexane. After phase separation and separation of the extractant from the crude product by distillation, the extractant can be used in other extraction operations.

Having now generally described this invention, a further understanding can be obtained by reference to certain specific examples which are provided herein for purposes of illustration only and are not intended to be limiting unless otherwise specified.

EXAMPLE 1

Preparation of Tetramethyl Orthocarbonate

A 72.2 g (0.5 mol) amount of trichloroacetonitrile was added dropwise over the course of 30 minutes to 360 g of a refluxing methanolic, 30% strength by weight sodium methoxide solution (2 mol) in a 1 liter four-necked flask fitted with paddle stirrer, internal thermometer, dropping funnel and condenser. The mixture was refluxed with stirring for a further 3 hours, and subsequently about 70% of the solvent was removed by distillation. After cooling, 624 g (0.55 mol) of an aqueous, 3% strength by weight hydrogen peroxide solution was added at room temperature. The reaction mixture was stirred for about 70 minutes, and 150 g of cyclohexane was then added. The separated organic phase was subsequently subjected to fractional distillation in a 50 cm Multifil packed column at a reflux ratio of 1:3. Tetramethyl orthocarbonate was obtained as a colorless liquid.

Yield: 49 g (72%)

Boiling point: 112° C.–114° C. (literature: 114° C.)

EXAMPLE 2

Preparation of Tetramethyl Orthocarbonate

In an apparatus as described in Example 1, a 72.2 g (0.5 mol) amount of trichloroacetonitrile was added dropwise over the course of 30 minutes to 360 g of a refluxing methanolic, 30% strength by weight sodium methoxide solution (2 mol). The mixture was refluxed with stirring for a further 3 hours, and about 80% of the solvent was subsequently removed by distillation. After cooling, 624 g (0.55 mol) of an aqueous, 3% strength by weight hydrogen peroxide solution was added at room temperature. The reaction mixture was stirred for about 60 minutes, and 150 g of methylcyclohexane was subsequently added. The separated organic phase was subsequently subjected to fractional distillation over a 50 cm Multifil packed column at a reflux ratio of 1:3. Tetramethylorthocarbonate was obtained as a colorless liquid.

Yield: 47 g (69%)

Boiling point: 110° C.–113° C. (literature: 114° C.)

EXAMPLE 3

Preparation of Tetraethyl Orthocarbonate

In an apparatus as described in Example 1, 36.2 g (0.25 mol) of trichloroacetonitrile was added dropwise over the course of 30 minutes to 324.3 g of a refluxing ethanolic, 21% strength by weight sodium ethoxide solution (1 mol). The mixture was refluxed with stirring for an additional 3 hours, and about 75% of the solvent were subsequently removed by distillation. After cooling, 397 g (0.35 mol) of an aqueous, 3% strength by weight hydrogen peroxide solution was added at room temperature. The reaction mixture was stirred for about 60 minutes, and 150 g of cyclohexane were subsequently added. The separated organic phase was subsequently subjected to fractional distillation over a 20 cm Multifil packed column. Tetraethyl orthocarbonate was obtained as a colorless liquid.

Yield: 40.8 g (85%)

Boiling point: 156° C.–158° C. (literature: 159° C.)

EXAMPLE 4

Preparation of Tetraethyl Orthocarbonate

In an apparatus as described in Example 1, 36.2 g (0.25 mol) of trichloroacetonitrile were added dropwise over the course of 30 minutes to 324.3 g of a refluxing ethanolic, 21% strength by weight sodium ethoxide solution (1 mol). The mixture was refluxed with stirring for an additional 3 hours, and about 65% of the solvent was subsequently removed by distillation. After cooling, 340 g (0.3 mol) of an aqueous, 3% strength by weight hydrogen peroxide solution was added at room temperature. The reaction mixture was stirred for about 50 minutes, and 200 g of toluene were subsequently added. The separated organic phase was subsequently subjected to fractional distillation over a 20 cm Multifil packed column. Tetraethyl orthocarbonate was obtained as a colorless liquid.

Yield: 39.9 g (83%)

Boiling point: 157° C.–158° C. (literature: 159° C.)

EXAMPLE 5

Preparation of Tetraisopropyl Orthocarbonate

In an apparatus as described in Example 1, 30 g (0.2 mol) of trichloroacetonitrile was added dropwise over the course of 40 minutes to a refluxing solution of 65.7 g (0.8 mol) of sodium isopropoxide dissolved in 400 g of isopropanol. The mixture was refluxed with stirring for an additional 3, hours, and about 80% of the solvent was subsequently removed by distillation. After cooling, 374 g (0.3 mol) of an aqueous, 3% strength by weight hydrogen peroxide solution was added at room temperature. The reaction mixture was stirred for about 80 minutes, and 150 g of toluene was subsequently added. The separated organic phase was subsequently subjected to fractional distillation over a 20 cm Multifil packed column. Tetraisopropyl orthocarbonate was obtained as a colorless liquid.

Yield: 22 g (45%)

Boiling point: 67° C.–69° C/10 mmHg (literature:

70° C./10 mmHg)

The disclosure of German application Ser. No. 10057198.0 filed Nov. 17, 2000 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letters Patent is:

1. A process for the preparation of orthocarbonates, comprising:

reacting trichloroacetonitrile with an alkali metal salt or alkaline earth metal salt of an alcohol of the formula:

$$R-OH \quad (II)$$

wherein R is an unsubstituted or substituted, saturated aliphatic or cycloaliphatic hydrocarbon radical in which the carbon atom of group R, linked to the oxygen atom of the alcohol, has at least one hydrogen atom, in a polar solvent;

reacting the product obtained in water with an oxidant selected from the group consisting of chlorine, chlorine water, a polysulfide, thiosulfate, polythionate, hydrogen peroxide, and hypochlorite or hypobromite solution;

extracting the organic-aqueous phase of the material obtained after oxidation; and distilling the extracted material obtained and obtaining orthocarbonate product of the formula:

$$C(OR)_4 \quad (I)$$

wherein each R group is as defined above.

2. The process as claimed in claim 1, wherein all or some of the solvent present during the reaction is removed by distillation after the reaction.

3. The process as claimed in claim 1, wherein the extraction is conducted with an organic solvent selected from the group consisting of aliphatic, cycloaliphatic, aromatic or chlorinated hydrocarbons, ketones and esters.

4. The process as claimed in claim 1, wherein the extractant is pentane or hexane.

5. The process as claimed in claim 1, wherein the extractant is cyclohexane, methylcyclohexane or ethylcyclohexane.

6. The process as claimed in claim 1, wherein the extractant is toluene, ethylbenzene, xylene, cumene or mesitylene.

7. The process as claimed in claim 1, wherein the extractant is dichloromethane, 1,1- or 1,2-dichloroethane or trichloromethane.

8. The process as claimed in claim 1, wherein the extractant is methyl isobutyl ketone, methylcyclohexanone or diisobutyl ketone.

9. The process as claimed in claim 1, wherein the extractant is ethyl acetate, butyl acetate or ethyl propionate.

10. The process as claimed in claim 1, wherein the extraction is conducted at a temperature ranging from 0° C. to 100° C.

11. The process as claimed in claim 1, wherein group R is methyl, ethyl, propyl, isopropyl, butyl, isobutyl, pentyl, isopentyl, neopentyl, cyclopropyl, cyclobutyl, cyclopentyl, cyclohexyl, cyclopropylmethyl, cyclopentylmethyl or cyclohexylmethyl.

12. The process as claimed in claim 1, wherein the polar solvent is tetrahydrofuran, dimethoxyethane, diisopropyl ether, dibutyl ether, diethylene glycol dimethyl ether, dimethyl sulfoxide, sulfolane, 2-methylsulfolane, 3-methylsulfolane, 2-methyl-4-butylsulfolane, acetonitrile, dimethylformamide or N,N-dimethylacetamide.

13. The process as claimed in claim 1, wherein the reaction temperature ranges from −20° C. to 200° C.

14. The process as claimed in claim 13, wherein the reaction temperature ranges from 50° C. to 150° C.

15. The process as claimed in claim 1, wherein the pressure of the reaction ranges from 0.1 to 50 bar.

* * * * *